United States Patent
Bara et al.

(10) Patent No.: US 6,426,079 B1
(45) Date of Patent: Jul. 30, 2002

(54) WATER-IN-OIL EMULSION, COMPOSITION COMPRISING SUCH AN EMULSION, AND USE THEREOF

(75) Inventors: Isabelle Bara, Paris; Patricia Lemann, Creteil; Florence Tournilhac, Paris; Annick Collette, Choisy le Roi; Jean-Christophe Simon, Paris, all of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/277,207

(22) Filed: Mar. 26, 1999

(30) Foreign Application Priority Data

Mar. 26, 1998 (FR) .............................. 98 03762

(51) Int. Cl.$^7$ ................................. B01F 3/08
(52) U.S. Cl. ..................... 424/401; 424/63; 424/64; 424/70.7; 424/70.12; 516/23; 514/938
(58) Field of Search ............... 424/401, 63, 64, 424/70.7, 70.12; 514/938; 516/23

(56) References Cited

U.S. PATENT DOCUMENTS

| | | | |
|---|---|---|---|
| 4,698,178 A | | 10/1987 | Hüttinger et al. |
| 4,999,418 A | | 3/1991 | Krutak et al. |
| 5,030,708 A | | 7/1991 | Krutak et al. |
| 5,032,670 A | | 7/1991 | Parham et al. |
| 5,043,376 A | | 8/1991 | Sharma et al. |
| 5,102,980 A | | 4/1992 | Krutak et al. |
| 5,104,913 A | | 4/1992 | Sharma et al. |
| 5,106,942 A | | 4/1992 | Krutak et al. |
| 5,194,463 A | | 3/1993 | Krutak et al. |
| 5,262,087 A | * | 11/1993 | Tachibana et al. .......... 252/309 |
| 5,281,659 A | | 1/1994 | Weaver et al. |
| 5,523,091 A | * | 6/1996 | Pastour et al. ............... 424/401 |
| 5,804,719 A | | 9/1998 | Didelot et al. |

FOREIGN PATENT DOCUMENTS

| | | | |
|---|---|---|---|
| EP | 0 331 833 | | 5/1988 |
| EP | 0 373 661 | | 6/1990 |
| EP | 374 332 | * | 6/1990 |
| EP | 0 583 130 | | 2/1994 |
| EP | 0 612 517 | | 8/1994 |
| EP | 0 719 540 | | 7/1996 |
| EP | 0 749 747 | | 12/1996 |
| EP | 0 787 485 | | 8/1997 |
| EP | 0 796 615 | | 9/1997 |
| EP | 0 819 419 | | 1/1998 |
| EP | 0 819 426 | | 1/1998 |
| GB | 2 294 392 | | 5/1996 |
| WO | WO 92/07913 | | 5/1992 |
| WO | WO 93/14742 | | 8/1993 |

OTHER PUBLICATIONS

English language Derwent Abstract of EP 0 719 540.
English language Derwent Abstract of EP 0 796 615.
English language Derwent Abstract of EP 0 749 747.
English language Derwent Abstract of EP 0 787 485.
English language Derwent Abstract of EP 0 819 419.
English language Derwent Abstract of EP 0 819 426.
Derwent Publication 86–288910 (JP 61 212321).

* cited by examiner

Primary Examiner—Margaret G. Moore
(74) Attorney, Agent, or Firm—Finnegan Henderson Farabow Garrett & Dunner, L.L.P.

(57) ABSTRACT

The present invention relates to a stable water-in-oil emulsion for cosmetic, pharmaceutical or hygiene use, comprising an aqueous phase and a fatty phase comprising a silicone oil, characterized in that it comprises an emulsifying system comprising at least one α,ω-substituted oxyalkylenated silicone of formula (I):

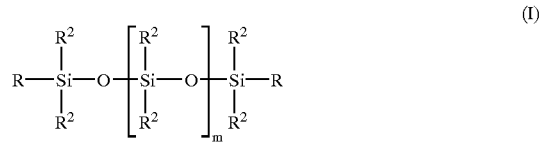

in which: $R = -(CH_2)_pO-(C_2H_4O)_x(C_3H_6O)_yR^1$ where:
  $R^1$ represents H, $CH_3$ or $CH_2CH_3$,
  p is an integer ranging from 1 to 5, x ranges from 1 to 100 and y ranges from 1 to 50,
  it being possible for the units $(C_2H_4O)$ and $(C_3H_6O)$ to be distributed randomly or in blocks,
  the $R^2$ radicals represent a $C_1$–$C_3$ alkyl radical or a phenyl radical,
  $5 \leq m \leq 300$,
and a co-surfactant chosen from the family of glycol mono- and/or diesters and glyceryl mono-, di- and/or triesters, and mixtures thereof. The invention also relates to a composition comprising the above emulsion, and to its applications in the cosmetics, pharmaceutical, dermatological or hygiene fields.

62 Claims, No Drawings

WATER-IN-OIL EMULSION, COMPOSITION COMPRISING SUCH AN EMULSION, AND USE THEREOF

The present invention relates to water-in-oil (W/O) emulsions, to compositions for cosmetic, pharmaceutical, hygiene or dermatological use, comprising such an emulsion, as well as to their use in the cosmetic, pharmaceutical, dermatological and/or hygiene fields.

These compositions may constitute care products for the skin, including the scalp, and/or make-up products for the skin, mucous membranes (the inside of the eyelids), semi-mucous membranes (lips), keratin fibres (hair, eyelashes, nails) or alternatively make-up products for the body.

Make-up compositions, in particular foundations, are generally in the form of a more or less fluid cream comprising fatty substances such as oils and a particulate phase generally composed of fillers and pigments.

It is generally sought to introduce into the fatty phase compounds such as silicones, which provide softness and fluidity. However, it is known that as the silicone oil content increases, it is more difficult to obtain a stable W/O emulsion, not only over time but also when it is subjected to large variations in temperature. In fact, the fluidity of the formula can be the cause of phenomena of instability over time, such as the release of oil at the surface, sedimentation of the pigments, thickening, etc.

With the aim of reducing these phenomena, it has been proposed in U.S. Pat. No. 4,698,178 to use a new class of silicone surfactants associated with polyols for the low temperatures, and with electrolytes or with metal soaps for the high temperatures.

The improvement in the stability of W/O emulsions has also been studied in patent application EP 331,833, which describes the use of oxyalkylenated silicones combined with water-swellable inorganic clays, and in patent application EP-A-612,517, which recommends the use of a combination of a silicone containing oxyalkylene groups and pendant alkyls with a gelling and/or thickening agent.

Nevertheless, when these compositions are applied to the skin, mucous membranes or semi-mucous membranes, they have the disadvantage of transferring to another surface. This means that the composition, once applied, is liable to be deposited, at least partly, on certain supports with which it is placed in contact, such as, for example, a glass, an item of clothing or the skin.

Once deposited, the said composition leaves a trace on the said support. This thus results in mediocre staying power of the composition on the skin or the mucous membranes, thus making it necessary to regularly renew its application.

Moreover, the appearance of unacceptable traces of the composition on certain items of clothing, and in particular on shirt collars, can discourage women from using this type of make-up.

Another disadvantage of these compositions lies in the problem of migration. Specifically, it has been found that certain compositions have a tendency to diffuse or migrate inside the fine lines and/or wrinkles on the skin, in the case of foundations; in the fine lines surrounding the lips, in the case of lipsticks; and in the folds of the eyelids, in the case of eyeshadows. The appearance of lines in the make-up, generated by the movements of the eyelids, has also been found, in particular in the case of eyeshadows. All of these phenomena generate a displeasing effect which, needless to say, it is desired to avoid.

The aim of the present invention is to provide a water-in-oil emulsion which has good stability, while at the same time retaining good cosmetic properties. In particular, it is desired to have available a stable water-in-oil emulsion which does not transfer after it has been used, in particular on the skin.

It has now been discovered, surprisingly and unexpectedly, that by using a specific emulsifying system, it is possible to obtain W/O emulsions which are not only stable over time, but are also stable with respect to variations in temperature, and which also show excellent cosmetic properties, as well as good resistance to transfer.

A subject of the present invention is thus a water-in-oil emulsion, comprising an aqueous phase and a fatty phase comprising a silicone oil, characterized in that it comprises an emulsifying system comprising at least one α,ω-substituted oxyalkylenated silicone of formula (I):

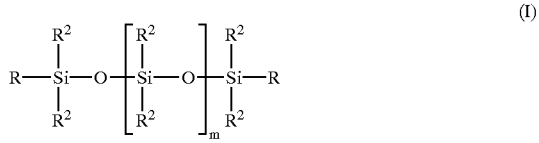

(I)

in which: $R = -(CH_2)_p O - (C_2H_4O)_x (C_3H_6O)_y R^1$ where: $R^1$ represents H, $CH_3$ or $CH_2CH_3$, p is an integer ranging from 1 to 5, x ranges from 1 to 100 and y ranges from 1 to 50, it being possible for the units $(C_2H_4O)$ and $(C_3H_6O)$ to be distributed randomly or in blocks, the $R^2$ radicals represent a $C_1$–$C_3$ alkyl radical or a phenyl radical, $5 \leq m \leq 300$, and a co-surfactant chosen from the family of glycol mono- and/or diesters and glyceryl mono-, di- and/or triesters, and mixtures thereof.

For the purposes of the invention, the term "co-surfactant" refers to an amphiphilic compound, i.e. a compound comprising both a lipophilic part (apolar part) and a hydrophilic part (polar part) and which can be adsorbed onto a surface or an interface.

Another subject of the invention relates to a composition, in particular a cosmetic, dermatological, pharmaceutical or hygiene composition, comprising an emulsion as defined above.

The invention also relates to a non-therapeutic treatment process for the skin and/or keratin fibres, in particular a make-up process, which comprises applying an emulsion and/or a composition as defined above to the skin and/or to the keratin fibres.

Another subject of the invention relates to the use of an emulsifying system as defined above, for preventing, limiting and/or reducing the transfer and/or migration of a cosmetic, dermatological, hygiene and/or pharmaceutical composition, in particular a make-up and/or care composition for the skin, mucous membranes or semi-mucous membranes.

Another subject of the invention relates to a process for limiting, reducing and/or preventing the transfer of a cosmetic, dermatological, hygiene and/or pharmaceutical composition, in particular a make-up and/or care composition for the skin, mucous membranes, semi-mucous membranes and/or keratin fibres, this process comprises introducing an emulsifying system as described above into the said composition.

The W/O emulsion according to the invention fully satisfies the stability standards, i.e.:

resistance to the centrifugation test at 4000 rpm for 1 hour, resistance to aging for 2 months at room temperature (25° C.) as well as at 45° C., resistance to 8 successive cycles of 8 hours each, where the temperatures of each cycle range from −20° C. to +20° C.

The emulsion according to the invention satisfies the following criteria:

it has and retains over the course of these tests a uniform and stable macroscopic and microscopic appearance (finely dispersed globules, absence of release) and its viscosity is constant over time.

The emulsion according to the invention also has very good resistance to transfer. Furthermore, the emulsion applied to the skin has the advantage of not migrating or diffusing in the folds of the skin in particular on the eyelids and/or the wrinkles on the face, in particular on the lips and on the eyes, and the contours of these areas (crow's feet).

It has been found that the emulsion used according to the invention applies and spreads easily and homogeneously, without leaving a greasy sensation, and has good cosmetic properties. The film obtained also has a light texture and remains comfortable to wear throughout the day.

Moreover, it is possible to add other adjuvants to the emulsion according to the invention, such as oils and/or powders (pigments and/or fillers), while at the same time retaining a stable emulsion. The emulsion is thus compatible with a large number of cosmetic adjuvants.

The emulsion according to the invention moreover has good sensory qualities, in particular great ease of application, comfort, softness, a good matte effect and good coverage, uniformity and staying power.

The emulsions of the invention comprise an emulsifying system comprising a specific α,ω-substituted oxyalkylenated silicone.

Throughout the text hereinabove and hereinbelow, the term "silicone" is intended to denote, in accordance with general acceptance, any organosilicon polymers or oligomers of linear or cyclic, branched or crosslinked structure, of variable molecular weight, obtained by polymerization and/or polycondensation of suitably functionalized silanes, and comprising a repetition of main units in which the silicon atoms are connected together via oxygen atoms (siloxane bond≡Si—O—Si≡), optionally substituted hydrocarbon-based radicals being linked directly via a carbon atom onto the said silicon atoms. The hydrocarbon-based radicals which are most common are alkyl radicals, especially $C_1$–$C_{10}$ alkyl radicals and in particular methyl, fluoroalkyl radicals, aryl radicals and in particular phenyl. They can be substituted, for example, with $C_1$–$C_{40}$ ester or ether groups or $C_7$–$C_{60}$ aralkyl groups.

Thus, the α,ω-substituted oxyalkylene silicone which may be used according to the invention is an organosilicon polymer as defined above, of linear structure, substituted at the two ends of the main chain with oxyalkylene groups connected to the Si atoms via a hydrocarbon-based group.

The α,ω-substituted oxyalkylenated silicone which can be used according to the invention corresponds to the general formula (I) below:

$$R-\underset{R^2}{\overset{R^2}{\underset{|}{\overset{|}{Si}}}}-O-\left[\underset{R^2}{\overset{R^2}{\underset{|}{\overset{|}{Si}}}}-O\right]_m-\underset{R^2}{\overset{R^2}{\underset{|}{\overset{|}{Si}}}}-R \quad (I)$$

in which: R=—$(CH_2)_pO$—$(C_2H_4O)_x(C_3H_6O)_yR^1$ where: $R^1$ represents H, $CH_3$ or $CH_2CH_3$, p is an integer ranging from 1 to 5, x ranges from 1 to 100 and y ranges from 1 to 50, it being possible for the units ($C_2H_4O$) and ($C_3H_6O$) to be distributed randomly or in blocks, the $R^2$ radicals represent a $C_1$–$C_3$ alkyl radical or a phenyl radical, and $5 \leq m \leq 300$.

Preferably, the α,ω-substituted oxyalkylenated silicone used according to the present invention corresponds to the general formula (I) for which all of the $R^2$ radicals are methyl radicals and:

p ranges from 2 to 4, x ranges from 3 to 100, m ranges from 50 to 200.

Preferably also, the average molecular weight of R ranges from 800 to 2600.

Preferably, the weight ratio of the $C_2H_4O$ units relative to the $C_3H_6O$ units ranges from 100:10 to 20:80.

Preferably, this ratio is about 42/58.

Preferably also, $R^1$ is a methyl group.

Even more preferably, the emulsion according to the invention comprises the α,ω oxyalkylenated silicone of the following formula:

$$R-\underset{CH_3}{\overset{CH_3}{\underset{|}{\overset{|}{SiO}}}}-\left[\underset{CH_3}{\overset{CH_3}{\underset{|}{\overset{|}{Si}}}}-O\right]_m-\underset{CH_3}{\overset{CH_3}{\underset{|}{\overset{|}{Si}}}}-R$$

in which:

m=100,

R=$(CH_2)_3$—O—$(C_2H_4O)_x$—$(C_3H_6O)_y$—$CH_3$, where x ranges from 3 to 100 and y ranges from 1 to 50, the weight ratio of $C_2H_4O$ units to $C_3H_6O$ units being about 42/58, the average molecular weight of R ranging from 800 to 1000.

The α,ω-substituted oxyalkylenated silicone as defined above is used according to the invention in a proportion ranging from 0.1 to 30%, preferably from 0.5 to 10%, by weight relative to the total weight of the emulsion.

Among the commercial products which can contain all or some of the α,ω-substituted oxyalkylenated silicones which may be used according to the invention as emulsifier are those sold under the names "Abil EM 97" by the company Goldschmidt or "KF 6009", "X22-4350", "X22-4349" or "KF 6008" by the company Shin Etsu.

The emulsifying system in the emulsions according to the invention also comprises a co-surfactant chosen from glycol mono- and/or diesters and glyceryl mono-, di- and/or triesters, and/or mixtures thereof.

Preferably, the co-surfactant has a HLB (Hydrophilic-Lipophilic Balance) of 7 or less.

Preferably, this co-surfactant is chosen from fatty acid esters of glycol and/or of glycerol such as glyceryl stearate, acetylated ethylene glycol stearate and isostearyl diglyceryl succinate.

Co-surfactants of this type are, for example the product sold by the company Hüls under the name "Imwitor 780K", which is an isostearyl diglyceryl succinate.

Mention may also be made of the product sold under the name "Unitwix" by the company United Guardian, which is a product comprising a mixture of fatty acid esters of glycerol and of glycol in a ratio of between 75/25 and 95/5% by weight, the said fatty acids being $C_{16}$–$C_{36}$, at least 50% of the said fatty acids being $Cl_8$–$C_{22.}$ Preferably, the co-surfactant is present in the emulsions and the compositions according to the invention in a proportion ranging from 0.05% to 10%, more preferably in a proportion ranging from 0.2% to 5%.

The fatty phase of the emulsions according to the invention comprises at least one volatile or non-volatile silicone oil.

The silicone oil which may be used according to the invention may be a linear, optionally functionalized or cyclic polydiorganosiloxane or an optionally crosslinked organopolysiloxane, or a mixture thereof.

The optionally functionalized linear polydiorganosiloxanes which may be used according to the invention correspond to the following general formula:

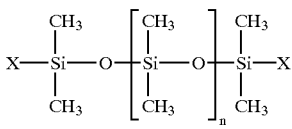

in which:

X is —$CH_3$ or OH and n is an integer ranging from 0 to 2000.

Among these, mention will be made in particular of the products sold under the name "AK" by the company Wacker, "SF" by the company General Electric and "Abil" by the company Goldschmidt, such as the product "Abil 10".

As cyclic polydiorganosiloxanes according to the invention, it is possible to use, alone or as a mixture, cyclomethicones of formula:

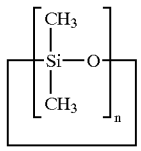

in which:

n is an integer from 3 to 8.

Among the cyclomethicones which are particularly preferred, mention will be made of cyclotetradimethylsiloxane (n=4), cyclopentadimethylsiloxane (n=5) and cyclohexadimethylsiloxane (n=6).

It is possible in particular to use the products sold under the names "DC Fluid 244", "DC Fluid 245", "DC Fluid 344" and "DC Fluid 345" by the company Dow Corning.

Other cyclomethicones which may be used according to the invention are those sold under the names "Abil K4" by the company Goldschmidt; "Silbione 70045 V2" and "Silbione Oil 70045 V5" by the company Rhone-Poulenc; as well as "Volatile Silicone 7158" and "Volatile Silicone 7207" by the company Union Carbide.

Preferably, volatile silicone oils, including cyclomethicones, are used.

As indicated above, the silicone oil used according to the invention is preferably present in a proportion of at least 5%, and preferably ranging from 25 to 45%, by weight relative to the total weight of the emulsion.

The compositions of the invention may also comprise other silicone compounds.

Among these silicone compounds are poly($C_1$–$C_{20}$) alkylsiloxanes, including phenylsilicone oils, as well as silicone gums and silicone waxes.

The silicone gums which may be used in the composition of the invention may be polysiloxanes with a high molecular mass, from about 200,000 to about 1,000,000, and with a dynamic viscosity of greater than 500,000 mPa·s. They may be used alone or as a mixture with a solvent such as a polydimethylsiloxane or polyphenylsiloxane oil, or a cyclomethicone.

The gums may be present in an amount up to 5% by weight of active material in the final composition, preferably up to 1%.

The silicone waxes which may be used in the composition according to the invention may be substituted linear polysiloxanes, for example, polyether silicone waxes and alkyldimethicones or alkoxydimethicones containing from 16 to 45 carbon atoms. These silicone waxes may be present in a proportion ranging from 0 to 15% by weight in the final composition, preferably in a proportion ranging from 2 to 10%.

The emulsions according to the invention may also comprise silicone resins comprising a combination of the units $R_3SiO_{1/2}$, $R_2SiO_{2/2}$, $RSiO_{3/2}$ and $SiO_{4/2}$.

The compositions according to the invention may also comprise non-silicone fatty substances, including pasty fatty substances, gums and waxes of plant, mineral, animal or synthetic origin.

The pasty fatty compounds may be defined with the aid of at least one of the following physicochemical properties:

having a viscosity ranging from 0.1 to 40 Pa·s (1 to 400 poises), measured at 40° C. with a Contraves TV rotary viscometer fitted with an MS-r3 or MS-r4 rotor at a frequency of 60 Hz, or having a melting point ranging from 25 to 70° C., preferably from 25 to 55° C.

Preferred non-silicone waxes which may be used in the invention are waxes of animal origin, such as lanolin, beeswax, spermaceti, lanolin derivatives such as lanolin alcohols and hydrogenated, hydroxylated or acetylated lanolin, lanolin fatty acids and acetylated lanolin alcohol; waxes of plant origin, such as carnauba wax, candelilla wax, kapok wax, ouricury wax, rice wax, hydrogenated jojoba wax, alfalfa wax, Japan wax, cork fibre waxes or sugar cane wax, or even cocoa butter; mineral waxes, for example paraffin wax, montan wax, lignite wax, petrolatum wax, petroleum jelly wax or microcrystalline waxes, ceresin or ozokerite; synthetic waxes, such as polyethylene waxes, the waxes obtained by Fischer-Tropsch synthesis and linear esters resulting from the reaction of a saturated $C_{10}$ to $C_{40}$ carboxylic acid and a saturated $C_{10}$ to $C_{40}$ alcohol, such as myristyl myristate. Cetyl alcohol, stearyl alcohol, calcium lanolates or stearates, castor oil, palm oil, coconut oil, sunflower oil or hydrogenated coconut oil may also be used.

The fatty phase of the W/O emulsion according to the invention may comprise one or more hydrocarbon-based oil(s) in a proportion which can be up to 40% by weight relative to the total weight of the fatty phase of the emulsion.

A preferred hydrocarbon-based oil is any fluid oil (or mixture of oils) which is stable at the usual temperature at which the cosmetic, pharmaceutical or hygiene products are used, such as oils of plant, animal, mineral or synthetic origin, fluoro oils and triglycerides of $C_{12}$–$C_{18}$ fatty acids.

Preferred oils of plant or animal origin, which may be modified or unmodified are, for example, sweet almond oil, avocado oil, castor oil, olive oil, jojoba oil, sunflower oil, wheat germ oil, sesame oil, groundnut oil, grape seed oil, soybean oil, rapeseed oil, safflower oil, coconut oil, corn oil, hazelnut oil, karite butter, palm oil, (apricot) kernel oil or beauty-leaf oil.

Preferred oils of mineral origin are, for example, liquid paraffin.

Preferred synthetic oils are, in particular, volatile or non-volatile isoparaffins and polyisobutenes.

These fatty substances may be chosen in particular by a person skilled in the art so as to prepare a composition having the desired properties, for example in terms of consistency or texture. They are preferably used at a content of less than or equal to 7% by weight relative to the total weight of the emulsion, in order to preserve the advantageous properties of the emulsion used according to the invention.

Other liposoluble adjuvants which may be incorporated into the fatty phase are lipophilic UV screening agents, lipophilic vitamins, antioxidants, fragrances and ceramides.

The aqueous phase of the emulsion according to the invention may comprise water or a floral water such as cornflower water.

In addition, the aqueous phase may comprise from 0% to 14% by weight, relative to the total weight of the aqueous phase, of a lower $C_2$–$C_6$ monoalcohol and/or a polyol such as glycerol, butylene glycol, isoprene glycol or propylene glycol.

The aqueous phase may also contain adjuvants commonly used in cosmetic W/O emulsions, for example, lubricants, moisturizers such as glycerol and propylene glycol, trace elements, hydrophilic UV screening agents and polysaccharides, as well as electrolytes such as NaCl or $MgSO_4$. The aqueous phase may also comprise active principles such as plant extracts, bacterial extracts, proteins or protein hydrolysates, and in particular hydrolysates of collagen or of elastin.

These active principles may be present in a proportion ranging from 1 to 15%.

Depending on the texture desired for the emulsion according to the invention, the proportion of the dispersed aqueous phase may range from 35% to 80%.

In general, the emulsion according to the invention may comprise from 30% to 55% by weight of fatty phase, from 5% to 12% by weight of surfactant, and from 35% to 75% by weight of aqueous phase.

In addition, the emulsion according to the invention may comprise one or more co-surfactants and one or more thickeners in concentrations preferably ranging from 0 to 6% by weight, relative to the total weight of the emulsion.

The thickener may be chosen from modified clays such as modified magnesium silicate (bentone gel VS38 from Rheox) or hectorite modified with distearyldimethylammonium chloride (bentone 38 CE from Rheox).

Advantageously, the emulsion according to the invention is substantially free of thickener.

The emulsion according to the invention may also comprise pearlescent agents, pigments and/or fillers usually used in cosmetic compositions.

The pigments may be present in the emulsion in a proportion ranging from 0 to 20% by weight, relative to the total weight of the emulsion, and preferably in a proportion ranging from 2 to 15%. They may be white or coloured, and inorganic and/or organic. Preferred inorganic pigments are titanium dioxide, zirconium dioxide or cerium dioxide, as well as zinc oxide, iron oxide or chromium oxide, ferric blue, pearlescent agents such as mica coated with titanium oxide, with iron oxide, with natural pigment or with bismuth oxychloride, as well as coloured titanium mica. Preferred organic pigments are, for example, carbon black, and barium, strontium, calcium and aluminium lakes. The pigments may also have a hydrophobic surface or may be treated so as to make their surface hydrophobic; this treatment may be carried out according to the methods known to those skilled in the art; in particular, the pigments may be coated with silicone compounds such as PDMSs and/or with polymers, in particular polyethylenes and/or amino acids.

Preferred coated pigments are, for example, the pigments sold under the name "Covasil" by the company Wacker (pigments containing triisostearyl titanate).

The pigments thus coated can be incorporated into the emulsion according to the invention in a proportion ranging from 0.1 to 15% by weight relative to the total weight of the emulsion.

The fillers, which may be present in the emulsion in a proportion ranging from 0 to 20% by weight relative to the total weight of the emulsion, preferably from 0 to 10%, may be mineral or synthetic, and lamellar or non-lamellar. Preferred fillers are, for example, talc, mica, silica, kaolin, Teflon, starch, natural mother-of-pearl, boron nitride, microspheres such as Expancel (Nobel Industrie), or microsponges such as Polytrap (Dow Corning). Preferably, spherical fillers which are less than 25 μm in size are used, such as polyethylene powders, Nylon powders, microbeads of silicone resin (Tospearis from Toshiba) or silica microspheres, it being possible for these fillers to contribute towards improving the transfer-resistance properties of the emulsions of the invention.

In a preferred form of the invention, the emulsion comprises fillers having an average particle size equal to 15 microns or less. Preferably, these fillers are non spherical. Preferably, the weight ratio of the fillers to the oils, in the composition applied on the skin and after evaporation of the volatile oils, is from 30:70 to 50:50. More preferably, if n, represents the average refractive index of the totality of the fillers and if $n_2$ represents the average refractive index of the totality of the oils, then:

$$0<|n_1-n_2|\leq 0.3$$

and preferably, $$0<|n_1-n_2|\leq 0.15.$$

Thus, it is possible to obtain a foundation comprising very few pigments and still concealing the skin microreliefs. This composition shows soft-focus properties, in other words, it gives a blurred effect which conceals the skin microreliefs.

The emulsion according to the invention may also comprise a film-forming compound.

Thus the emulsion according to the invention may comprise polymers in aqueous dispersion, such as, for example, acrylic polymers, polyesters and/or polyurethanes in aqueous dispersion. For example, the emulsion may comprise a vinyl acetate/vinyl p-tert-butylbenzoate/crotonic acid copolymer as a stabilized, partially neutralized aqueous dispersion.

The emulsion according to the invention may also comprise a dispersion of polymer particles in a non-aqueous medium, as described, for example, in document EP 749, 747.

The emulsion according to the invention may also comprise a cosmetically, pharmaceutically or hygienically acceptable medium. In this case, it may comprise any additive usually used in the field of cosmetics, pharmaceuticals or hygiene, such as antioxidants, dyes, fragrances, essential oils, preserving agents, cosmetic active agents, moisturizers, vitamins, sphingolipids, liposoluble polymers, in particular hydrocarbon-based polymers, such as polybutene, polyalkylenes, polyacrylates and silicone polymers which are compatible with the fatty substances.

These additives may be present in the composition in a proportion ranging from 0 to 10% by weight.

Needless to say, a person skilled in the art will take care to select optional complementary compounds, and/or the amount thereof, such that the advantageous properties of the composition according to the invention are not, or are not substantially, adversely affected by the addition envisaged.

The emulsions according to the invention may be in the form of a cosmetic product, and in particular in the form of a care product for the body and/or the face and/or the scalp, or alternatively a make-up product, in particular a foundation, a blusher, an eyeshadow, an eyeliner, a mascara or a lipstick.

They may also be in non-dyed form, optionally containing cosmetic active agents. The emulsion according to the invention may be in the form of a thickened emulsion, a fluid emulsion, a cream, a milk or a serum, which may be used as a care product or an antisun product.

Preferably, the emulsions according to the invention are in the form of a fluid.

The process for preparing the emulsions according to the invention comprised: (a) in a first stage, heating the fatty phase containing the emulsifying system up to a temperature which is sufficient to melt all of the constituents, preferably a temperature ranging from 60 to 85° C., and then incorporating the optional additional liposoluble adjuvants, and (b) in a second stage, after cooling the fatty phase to a temperature ranging from 40 to 60° C., adding the aqueous phase, brought to the same temperature, to the fatty phase with slow gentle stirring, and then, when the temperature has returned to about 25° C., subjecting the preparation to vigorous stirring.

This second step may also be carried out by addition of the aqueous phase to the fatty phase with vigorous stirring, the aqueous phase being brought to the same temperature as the fatty phase.

Several examples of cosmetic compositions in the form of W/O emulsions will now be given for illustrative purposes. In the examples which follow, the amounts are given as a percentage by weight relative to the total weight of the composition.

COMPARATIVE EXAMPLE

The Inventors prepared the following two emulsions A and B with similar dynamic viscosities (~500 mPa·s (500 cps) at T°=25° C.). These viscosities were measured with an RM180 Rheomat viscometer (Rheometric Scientific) with spindle No. 2, at a temperature of 25° C. and at a shear rate of 200 s$^{-1}$, at time t=10 minutes.

Emulsion A (in accordance with the invention):

| | |
|---|---|
| α, ω-substituted oxypropylenated oxyethylenated silicone/cyclomethicone mixture (85/15) sold under the trade name "Abil EM 97" by the company Goldschmidt | 6% |
| isostearyl diglyceryl succinate sold under the trade name "Imwitor 780 K" by the company Hüls | 2% |
| cyclomethicone | 25% |
| isododecane | 4.55% |
| pigment | 10% |
| Nylon powder | 8% |
| vinyl acetate/vinyl p-tert-butylbenzoate/crotonic acid copolymer as a stabilized, partially neutralized aqueous dispersion | 20% |
| diisopropyl adipate | 1% |
| water | qs 100% |

Emulsion B (comparative):

| | |
|---|---|
| silicone containing pendant alkyl, oxyethylene and oxypropylene groups in a mixture of polyglyceryl 4-isostearate and hexyl laurate, sold under the trade name "Abil WE 09" by the company Goldschmidt | 9% |
| mixture of acetylated glycol stearate and tristearine sold under the trade name "Unitwix" by the company Guardian | 0.5% |
| cyclomethicone | 25% |
| diphenyl dimethicone | 6% |
| isododecane | 4.55% |
| hectorite | 4% |
| pigment | 10% |
| Nylon powder | 8% |
| vinyl acetate/vinyl p-tert-butyl benzoate/crotonic acid copolymer as a stabilized, partially neutralized aqueous dispersion | 20% |
| diisopropyl adipate | 1% |
| water | qs 100% |

These emulsions were obtained according to the following preparation process:

the pigments were predispersed in some of the cyclomethicone.

The rest of the oil was homogenized with the surfactants (at a temperature ranging from 40 to 50° C. for emulsion B, without heating for emulsion A).

The mixture was left to cool. The pigments and the Nylon powder were added to this mixture (and the modified hectorite preswollen in a small amount of isododecane, for emulsion B).

All of the aqueous phase was added to the above fatty phase, at first with slow stirring, and then with vigorous stirring for 10 minutes.

The copolymer and the diisopropyl adipate were added, with slow stirring.

These two foundations have a creamy, light, soft texture. They are easy to apply to the skin and give the skin a velvety appearance. They feel very softny. They are comfortable to wear.

1) Evaluation of the Stability:

Emulsion A according to the invention has better stability after 1 month at T°=45° C. than emulsion B (for emulsion B, considerable release of oil at the surface of the emulsion and many signs of breakdown of the emulsion and of reaggregation of the pigments are observed by microscope), this being the case even in the absence of stabilizing compounds such as the silicone gum (diphenyl dimethicone) and the hectorite which are present in emulsion B.

2) Evaluation of the Transfer Resistance:

The Inventors evaluated the transfer resistance of these two compositions in the following way: emulsions A and B were applied comparatively per half-neck to a panel of 6 individuals. The products were then left to dry for 10 minutes. Neck bands were then applied for 30 minutes to each half-neck.

The results obtained are collated in the following table:

| Transfer | Emulsion A (invention) | Emulsion B (comparative) |
|---|---|---|
| None 0 | | |
| Traces 1 | | |
| Traces + 2 | | |
| Slight 3 | 3 | |
| Slight + 4 | 1 | 1 |
| Moderate 5 | 2 | 4 |
| Moderate + 6 | | 1 |
| Large 7 | | |
| SCORE (average) | 3.8 | 5 |

It emerges clearly from the above table that the composition according to the invention which comprises, as emulsifying system, a combination of α,ω-oxyalkylenated silicone with a glyceryl ester, transfers less than an emulsion of the prior art, which comprises a dimethicone copolyol; not in accordance with that of the invention with a glyceryl ester.

Composition Example

The Inventors made the following composition:

| | |
|---|---|
| lipophilic coated pigments | 3% |
| talc having an average particle size of less than 15 microns | 8% |
| magnesium sulfate | 0.7% |
| α-ω-substituted oxypropylenated oxyethylenated silicone/cyclomethicone mixture (85/15) sold under the trade name "Abil EM 97" by the company Goldschmidt | 6% |
| isostearyl diglyceryl succinate sold under the trade name "Imwitor 780 K" by the company Hüls | 2% |
| cyclomethicone | 25% |
| polydimethylsiloxane | 4% |
| isododecane | 4.5% |
| preservative | qs |
| water | qs 100% |

This composition, although containing very few pigments, conceals advantageously the skin microreliefs.

What is claimed is:

1. A water-in-oil emulsion, comprising an aqueous phase and a fatty phase comprising at least one silicone oil, said emulsion comprising an emulsifying system comprising at least one α,ω-substituted oxyalkenylated silicone of formula (I):

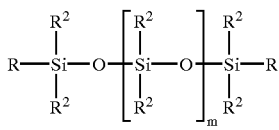

in which: $R=-(CH_2)_pO-(C_2H_4O)_x(C_3H_6O)_yR^1$ where:
$R^1$ represents H, $CH_3$ or $CH_2CH_3$,
p is an integer ranging from 1 to 5, x ranges from 1 to 100 and y ranges from 1 to 50,
the units $(C_2H_4O)$ and $(C_3H_6O)$ being distributed randomly or in blocks,
the $R^2$ radicals represent a $C_1-C_3$ alkyl radical or a phenyl radical,
$5 \leq m \leq 300$,
and at least one co-surfactant chosen from glycol monoesters, glycol diesters, glyceryl monoesters, glyceryl diesters, and glyceryl triesters, with the proviso that the glyceryl triesters are not chosen from glyceryl trioctanoate.

2. The emulsion according to claim 1, wherein said $R^2$ radicals are all methyl radicals and:
p ranges from 2 to 4,
x ranges from 3 to 100,
m ranges from 50 to 200.

3. The emulsion according to claim 1, wherein the average molecular weight of R ranges from 800 to 2600.

4. The emulsion according to claim 1, wherein the weight ratio of the $C_2H_4O$ units relative to the $C_3H_6O$ units ranges from 100:10 to 20:80.

5. The emulsion according to claim 4, wherein said weight ratio is about 42/58.

6. The emulsion according to claim 1, wherein the $R^1$ is a methyl group.

7. The emulsion according to claim 1, wherein said oxyalkylenated silicone corresponds to the following formula:

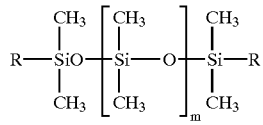

in which:
m=100,
$R=(CH_2)_3-O-(C_2H_4O)_x-(C_3H_6O)_y-CH_3$, where x ranges from 3 to 100 and y ranges 1 to 50, the weight ratio of $C_2H_4O$ units to $C_3H_6O$ units being about 42/58, the average molecular weight of R ranging from 800 to 1000.

8. The emulsion according to claim 1, wherein said oxyalkylenated silicone is present in the emulsion in a proportion ranging from 0.1 to 30% by weight relative to the total weight of the emulsion.

9. The emulsion according to claim 8, wherein said oxyalkylenated silicone is present in the emulsion in a proportion ranging from 0.5 to 10%.

10. The emulsion according to claim 1, wherein said co-surfactant is chosen from fatty acid esters of glycol and of glycerol.

11. The emulsion according to claim 10, wherein said fatty acid esters of glycol or of glycerol are chosen from glyceryl stearate, acetylated ethylene glycol stearate and isostearyl diglyceryl succinate.

12. The emulsion according to claim 11, wherein said co-surfactant is isostearyl glyceryl succinate.

13. The emulsion according to claim 1, wherein said co-surfactant is a mixture of fatty acid esters of glycerol and of glycol in a ratio ranging from 75/25 to 95/5% by weight, the said fatty acids being $C_{16}-C_{36}$, and at least 50% of the said fatty acids being $C_{18}-C_{22}$.

14. The emulsion according to claim 1, wherein said co-surfactant is present in a proportion ranging from 0.05% to 10% by weight, relative to the total weight of the emulsion.

15. The emulsion according to claim 14, wherein said co-surfactant is present in a proportion ranging from 0.2% to 5%.

16. The emulsion according to claim 1, wherein said at least one silicone oil is chosen from optionally functionalized linear polydiorganosiloxanes, cyclic polydiorganosiloxanes, and optionally crosslinked organopolysiloxanes.

17. The emulsion according to claim 16, wherein said polydiorganosiloxanes correspond to the following formula:

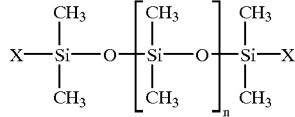

in which:
X is $-CH_3$ or OH, and
n is an integer ranging from 0 to 2000.

18. The emulsion according to claim 16, wherein said cyclic polydiorganosiloxanes are chosen from cyclomethicones and mixtures of cyclomethicones corresponding to the following formula:

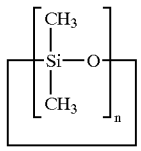

in which:

n is an integer from 3 to 8.

19. The emulsion according to claim 18, wherein said cyclomethicones are chosen from cyclotetradimethylsiloxane (n=4), cyclopentadimethylsiloxane (n=5) and cyclohexadimethylsiloxane (n=6).

20. The emulsion according to claim 16, wherein said at least one silicone oil is chosen from cyclic polydiorganosiloxanes.

21. The emulsion according to claim 16, wherein said at least one silicone oil is present in a proportion of at least 5% by weight relative to the total weight of the emulsion.

22. The emulsion according to claim 21, wherein said at least one silicone oil is present in a proportion ranging from 25 to 45%.

23. The emulsion according to claim 1, wherein said emulsion further comprises silicone compounds, different from said at least one silicone oil as defined in claim 1, chosen from poly($C_1$–$C_{20}$)alkylsiloxanes, silicone gums and silicone waxes.

24. The emulsion according to claim 23, wherein said silicone gums have a molecular mass ranging from about 200,000 to about 1,000,000, and with a dynamic viscosity of greater than 500,000 mPa·s.

25. The emulsion according to claim 23, wherein said silicone gums are present in an amount up to 5% by weight of active material in the final emulsion.

26. The emulsion according to claim 23, wherein said silicone gums are present in an amount up to 1%.

27. The emulsion according to claim 23, wherein said silicone waxes are substituted linear polysiloxanes.

28. The emulsion according to claim 27, wherein said substituted linear polysiloxanes are chosen from polyether silicone waxes, alkyldimethicones containing from 16 to 45 carbon atoms, and alkoxydimethicones containing from 16 to 45 carbon atoms.

29. The emulsion according to claim 23, wherein said silicone waxes are present in a proportion up to 15% by weight of the final emulsion.

30. The emulsion according to claim 29, wherein said silicone waxes are present in an amount ranging from 2 to 10%.

31. The emulsion according to claim 1, wherein said emulsion further comprises at least one silicone resin comprising a combination of the units $R_3SiO_{1/2}$, $R_2SiO_{2/2}$, $RSiO_{3/2}$, and $SiO_{4/2}$.

32. The emulsion according to claim 1, wherein said emulsion further comprises at least one non-silicone fatty substance chosen from pasty fatty substances, gums, waxes of plant origin, waxes of mineral origin, waxes of animal origin, waxes of synthetic origin, oils of plant origin, oils of mineral origin, oils of animal origin, and oils of synthetic origin.

33. The emulsion according to claim 1, wherein said fatty phase comprises at least one hydrocarbon-based oil in an amount up to 40% by weight relative to the total weight of the fatty phase of the emulsion.

34. The emulsion according to claim 1, wherein said fatty phase further comprises lipophilic adjuvants chosen from lipophilic UV screening agents, lipophilic vitamins, antioxidants, fragrances and ceramides.

35. The emulsion according to claim 1, wherein said aqueous phase comprises water or a floral water.

36. The emulsion according to claim 1, wherein said aqueous phase comprises from 0 to 14% by weight, relative to the total weight of the aqueous phase, a lower $C_2$–$C_6$ monoalcohol or a polyol.

37. The emulsion according to claim 1, wherein said aqueous phase further comprises adjuvants and active principles.

38. The emulsion according to claim 37, wherein said active principles are present in a proportion ranging from 1 to 15%.

39. The emulsion according to claim 1, wherein said aqueous phase is present in an amount ranging from 35 to 80% of the total weight of the emulsion.

40. The emulsion according to claim 1, wherein said emulsion comprises from 30 to 55% by weight of fatty phase, from 5 to 12% by weight of surfactant, and from 35 to 75% by weight of aqueous phase.

41. The emulsion according to claim 1, wherein said emulsion further comprises at least one co-surfactant different from said at least one co-surfactant as defined in claim 1.

42. The emulsion according to claim 1, wherein said emulsion further comprises a particulate phase which comprises at least one ingredient selected from pigments, pearlescent agents, and fillers.

43. The emulsion according to claim 42, wherein said at least one pigment is present in an amount up to 20% by weight relative to the total weight of the emulsion.

44. The emulsion according to claim 43, wherein said at least one pigment is present in an amount ranging from 2 to 15%.

45. The emulsion according to claim 42, wherein said at least one filler is chosen from talc, mica, silica, kaolin, Teflon, starch, natural mother-of-pearl, boron nitride, microspheres, microsponges, polyethylene powders, Nylon powders, microbeads of silicone resin and silica microspheres.

46. The emulsion according to claim 42, wherein said at least one filler is present in an amount up to 20% by weight relative to the total weight of the emulsion.

47. The emulsion according to claim 46, wherein said at least one filler is present in an amount up to 10%.

48. The emulsion according to claim 42, wherein said at least one filler has an average particle size of 15 microns or less.

49. The emulsion according to claim 42, wherein said at least one filler is non spherical.

50. The emulsion according to claim 42, wherein the weight ratio of said at least one filler to said at least one silicone oil, in the emulsion applied on skin and after evaporation of any volatile oils in said emulsion, ranges from 30:70 to 50:50.

51. The emulsion according to claim 42, wherein $n_1$ represents the average refractive index of the totality of said at least one filler and $n_2$ represents the average refractive index of the totality of said at least one silicone oils and $$0<|n_1-n_2|\leq 0.3.$$

52. The emulsion according to claim 51, wherein $$0<|n_1-n_2|\leq 0.15.$$

53. The emulsion according to claim 1, wherein said emulsion further comprises a film-forming compound.

54. The emulsion according to claim 1, wherein said emulsion further comprises a cosmetically, pharmaceutically or hygienically acceptable medium.

55. The emulsion according to claim 1, wherein said emulsion further comprises additives present in a proportion up to 10% by weight relative to the total weight of the emulsion.

56. A composition for cosmetic, dermatological, pharmaceutical or hygiene use, wherein said composition comprises an emulsion according to claim 1.

57. The composition according to claim 56, wherein said composition is in the form of a cosmetic or care product for the body and/or the face and/or the scalp, or a make-up product, in the form of a foundation, a blusher, an eyeshadow, an eyeliner, a mascara or a lipstick.

58. The composition according to claim 57, wherein said composition is in the form of a thickened emulsion, a fluid emulsion, a cream, a milk or a serum.

59. The composition according to claim 58, wherein said composition is in the form of a fluid emulsion.

60. A process for the non-therapeutic treatment of the skin and/or keratin fibres, comprising applying an effective amount of an emulsion according to claim 1 and/or a composition containing an emulsion according to claim 1, to said skin and/or said keratin fibres.

61. A process for preventing or reducing the transfer or migration of a cosmetic, hygiene or pharmaceutical composition, comprising introducing into said composition an effective amount of an emulsifying system according to claim 1.

62. A process for reducing or preventing the transfer of a cosmetic, dermatological, hygiene and/or pharmaceutical composition, for the skin, mucous membranes, semi-mucous membranes and/or keratin fibres, said process comprising introducing an emulsifying system according to claim 1, into said composition.

* * * * *